United States Patent
Lee et al.

(10) Patent No.: US 11,058,359 B2
(45) Date of Patent: Jul. 13, 2021

(54) METHOD AND APPARATUS FOR REMOVING NOISE FROM MULTI-CHANNEL FNIRS

(71) Applicant: Daegu Gyeongbuk Institute of Science and Technology, Daegu (KR)

(72) Inventors: Gihyoun Lee, Daegu (KR); Sang Hyeon Jin, Daegu (KR); Jinung An, Daegu (KR)

(73) Assignee: DAEGU GYEONGBUK INSTITUTE OF SCIENCE AND TECHNOLOGY, Daegu (KR)

(*) Notice: Subject to any disclaimer, the term of this patent is extended or adjusted under 35 U.S.C. 154(b) by 571 days.

(21) Appl. No.: 16/028,678

(22) Filed: Jul. 6, 2018

(65) Prior Publication Data
US 2019/0083040 A1   Mar. 21, 2019

(30) Foreign Application Priority Data

Sep. 15, 2017  (KR) .................. 10-2017-0118853
Jun. 22, 2018  (KR) .................. 10-2018-0072348

(51) Int. Cl.
| | |
|---|---|
| *A61B 5/00* | (2006.01) |
| *G06N 3/08* | (2006.01) |
| *G16H 30/40* | (2018.01) |
| *G16H 40/63* | (2018.01) |
| *G16H 50/70* | (2018.01) |
| *G16H 30/20* | (2018.01) |
| *G06N 3/04* | (2006.01) |

(52) U.S. Cl.
CPC .......... *A61B 5/7207* (2013.01); *A61B 5/0075* (2013.01); *A61B 5/726* (2013.01); *A61B 5/7246* (2013.01); *G06N 3/04* (2013.01); *G06N 3/08* (2013.01); *G06N 3/084* (2013.01); *G16H 30/20* (2018.01); *G16H 30/40* (2018.01); *G16H 40/63* (2018.01); *G16H 50/70* (2018.01); *A61B 5/4064* (2013.01); *A61B 5/7264* (2013.01); *A61B 5/7267* (2013.01); *A61B 2562/046* (2013.01)

(58) Field of Classification Search
None
See application file for complete search history.

(56) References Cited

U.S. PATENT DOCUMENTS

| | | | |
|---|---|---|---|
| 9,848,812 B1* | 12/2017 | Harrivel | A61B 5/747 |
| 2010/0081903 A1* | 4/2010 | Izzetoglu | A61B 5/14553 |
| | | | 600/328 |
| 2020/0038653 A1* | 2/2020 | Sitaram | A61B 5/055 |

* cited by examiner

*Primary Examiner* — Jonathan Cwern
(74) *Attorney, Agent, or Firm* — Lex IP Meister, PLLC (57) ABSTRACT

Disclosed is a method of removing motion artifacts from functional near-infrared spectroscopy (fNIRS) signals. The method includes: disposing N optodes at a plurality of locations on a scalp, and forming a plurality of channels between the N optodes; calculating a correlation coefficient difference index of a neighbor channel around each receiver optode, and detecting a receiver optode in which a motion artifact has occurred based on the correlation coefficient difference index; and removing motion artifacts based on the detected receiver optode and an arrangement structure of the N optodes.

11 Claims, 8 Drawing Sheets

METHOD AND APPARATUS FOR REMOVING NOISE FROM MULTI-CHANNEL FNIRS

CROSS-REFERENCE TO RELATED APPLICATION(S)

This application claims priority to Korean Patent Application No. 10-2017-0118853, filed on Sep. 15, 2017, and Korean Patent Application No. 10-2018-0072348, filed on Jun. 22, 2018, in the Korean Intellectual Property Office, the disclosures of which are incorporated herein in their entirety by reference.

BACKGROUND

1. Field

One or more embodiments relate to a technique for removing motion artifacts from functional near-infrared spectroscopy (fNIRS) signals, and more particularly, to a technique for removing motion artifacts from fNIRS signals output by irradiating near-infrared signals to a plurality of locations of the brain based on channels formed between optodes disposed at the locations of the brain.

2. Description of the Related Art

In general, medical imaging apparatuses provide images by acquiring information about a patient. A magnetic resonance imaging (MRI) apparatus among the medical imaging apparatuses holds an important position in a diagnosis field using medical images since it has relatively undemanding photographing conditions and provides excellent contrast for soft tissues and various diagnosis information images. However, the MRI apparatus requires high cost and has spatial constraints, although it has high accuracy.

In order to compensate or solve the problems of the MRI apparatus, functional near-infrared spectroscopy (fNIRS) is used in gait and rehabilitation fields in which the MRI apparatus cannot be used. In the fNIRS, a method of removing motion artifacts from fNIRS signals using a wavelet description length detrending technique is used. However, the wavelet description length detrending technique considers only signal features of each single channel without considering the spatial features of multi-channel fNIRS signals. Accordingly, the wavelet description length detrending technique has a problem that it may attenuate or distort a hemodynamic response signal component of a channel signal in which no motion artifact occurs. In a single task-based experimental environment, there is a problem of determining a hemodynamic response component by a task as a motion artifact component and thus removing the hemodynamic response component.

Also, an electroencephalograpy (EEG) measuring method using fNIRS among invasive EEG measuring methods which are getting the spotlight lately can measure a walking training state in real time, however, the EEG measuring method has difficulties in acquiring integral EEG signals including neurophysiological information related to walking due to undesired noise, etc. caused by movements of head, body, etc.

SUMMARY

One or more embodiments include a technique for removing motion artifacts from functional near-infrared spectroscopy (fNIRS) signals.

One or more embodiments include a technique for removing motion artifacts from multi-channel fNIRS signals using a characteristic of an arrangement of channels.

One or more embodiments include a technique for removing motion artifacts from fNIRS signals using multi-channel wavelet transformation.

Additional aspects will be set forth in part in the description which follows and, in part, will be apparent from the description, or may be trained by practice of the presented embodiments.

According to an embodiment of the present disclosure, a method of removing motion artifacts from a multi-channel functional near-infrared spectroscopy (fNIRS) signal includes: disposing N optodes at a plurality of locations on a scalp; forming a plurality of channels between the N optodes, wherein each channel is connected to a transmitter optode and a receiver optode; calculating a first correlation coefficient and a second correlation coefficient for each channel, wherein the first correlation coefficient represents a correlation of the channel to the transmitter optode and the second correlation coefficient represents a correlation of the channel to the receiver optode; calculating a correlation coefficient difference index which is a difference between the first correlation coefficient and the second correlation coefficient, for each channel; calculating a sum of correlation coefficient difference indices of neighbor channels of each receiver optode; deciding a receiver optode Ropt having a greatest sum of correlation coefficient difference indices; selecting a channel having a greatest correlation coefficient difference index among channels around the receiver optode Ropt, as a channel in which a motion artifact has occurred; and removing motion artifacts from all neighbor channels of a transmitter optode around the selected channel.

The removing of the motion artifacts may include: performing wavelet transformation on the selected channel to obtain a weight for each wavelet band of the channel; applying a neural network to the selected channel to remove motion artifacts from the selected channel, and then training and deciding a weight for each wavelet band of the channel; and applying the decided weight variable for each wavelet band to neighbor channels of a transmitter optode around the selected channel, thereby removing motion artifacts.

The first correlation coefficient and the second correlation coefficient may be calculated based on an entropy value of each channel.

The first correlation coefficient may be calculated from neighbor channels around the transmitter optode, and represent a correlation between an entropy value of an arbitrary channel among the neighbor channels around a transmitter optode and a mean value of entropy values of the remaining neighbor channels except for the arbitrary channel among the neighbor channels around the transmitter optode, and the second correlation coefficient may be calculated from neighbor channels around the receiver optode, and represent a correlation between an entropy value of an arbitrary channel among the neighbor channels around a receiver optode and a mean value of entropy values of the remaining neighbor channels except for the arbitrary channel among the neighbor channels around the receiver optode.

According to another embodiment of the present disclosure, a method of removing motion artifacts from a multi-channel functional near-infrared spectroscopy (fNIRS) signal includes: disposing N optodes at a plurality of locations on a scalp;

forming a plurality of channels between the N optodes; calculating a correlation coefficient difference index of a neighbor channel around each receiver optode, and detecting a receiver optode in which a motion artifact has occurred based on the correlation coefficient difference index; and removing motion artifacts based on the detected receiver optode and an arrangement structure of the N optodes.

According to another embodiment of the present disclosure, an apparatus of removing motion artifacts from a multi-channel functional near-infrared spectroscopy (fNIRS) signal includes: an optode arrangement portion configured to dispose N optodes at a plurality of locations on a scalp; a channel portion configured to form a plurality of channels between the N optodes, wherein each channel is connected to a transmitter optode and a receiver optode; a correlation coefficient difference calculator configured to calculate a first correlation coefficient and a second correlation coefficient for each channel, and configured to calculate a correlation coefficient difference index which is a difference between the first correlation coefficient and the second correlation coefficient, for each channel, wherein the first correlation coefficient represents a correlation of the channel to the transmitter optode and the second correlation coefficient represents a correlation of the channel to the receiver optode; a receiver optode decider configured to calculate a sum of correlation coefficient difference indices of neighbor channels around each receiver optode, and to decide a receiver optode Ropt having a greatest sum of correlation coefficient difference indices; a motion artifact channel selector configured to select a channel having a greatest correlation coefficient difference index among channels around the receiver optode Ropt, as a channel in which a motion artifact has occurred; and a motion artifact remover configured to remove motion artifacts from all neighbor channels of a transmitter optode around the selected channel.

The motion artifact remover may include: a wavelet transformer configured to perform wavelet transformation on the selected channel to obtain a weight variable for each wavelet band of the channel; a trainer configured to apply a neural network to the selected channel to remove a motion artifact of the selected channel, and then to train and decide a weight variable for each wavelet band of the channel; and an applier configured to apply the decided weight variable for each wavelet band to neighbor channels of a transmitter optode around the selected channel, thereby removing motion artifacts.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Hereinafter, the present disclosure will be described with reference to the accompanying drawings.

Figure 1:
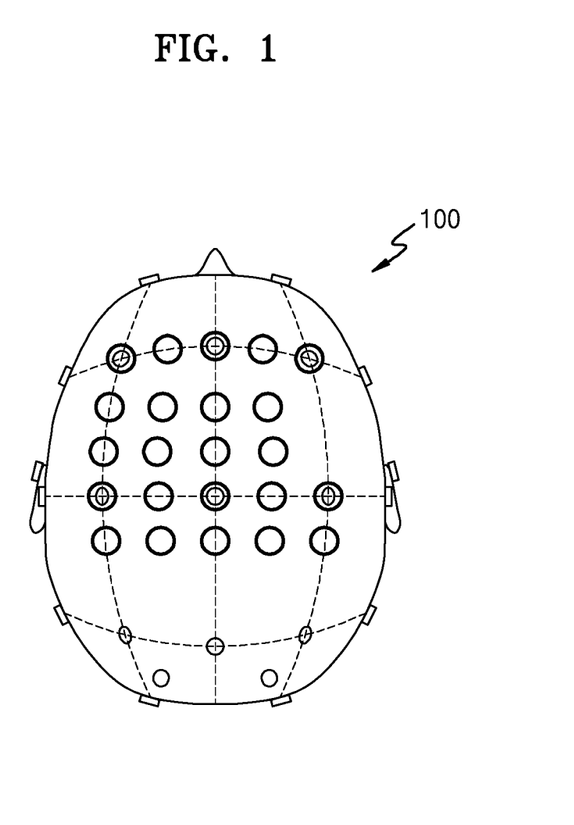
FIG. 1 shows an example of an arrangement of N optodes at a plurality of locations on a subject's scalp, according to an embodiment of the present disclosure.
Figure 2:
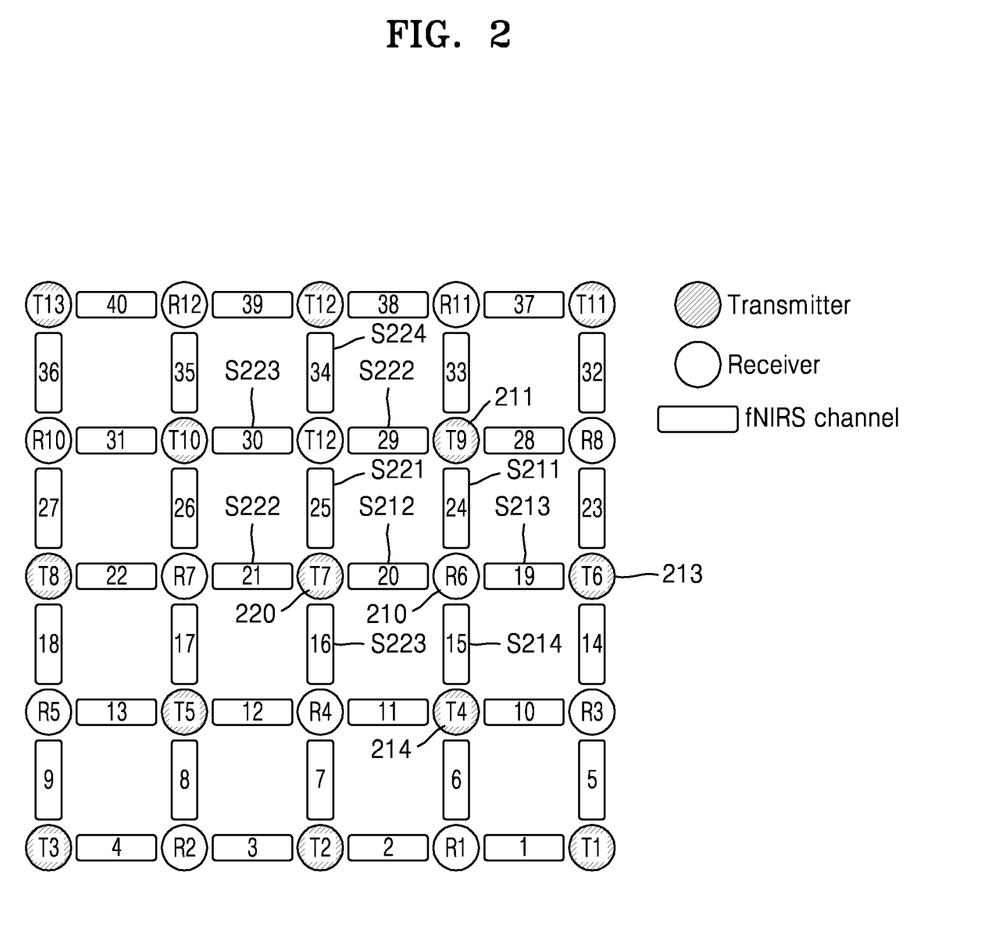
FIG. 2 shows an example of channels formed between N optodes, according to an embodiment of the present disclosure.

FIGS. 1 and 2 show an example in which N optodes are arranged at a plurality of locations on a subject's scalp and channels are formed between the optodes, according to an embodiment of the present disclosure.

Referring to FIGS. 1 and 2, fNIRS channels may almost cover the supplementary motor area (SMA) and primary motor cortex (M1) related to a walking task. Generally, the major reason of the motion artifact during the walking task using fNIRS signals may be dislocation of the optode and sway the optode cable. According to an embodiment of the present disclosure, when motion artifacts occur, a highly unbalanced optode may be detected from among optodes to thereby find an optode at which motion artifacts occur.

According to an embodiment of the present disclosure, channel information between optodes may be used to find a highly unbalanced optode. The operation will be described with reference to FIG. 2, below.

FIG. 2 shows optodes (T1 to T13 and R1 to R12) formed in a 5×5 structure, according to an embodiment of the present disclosure, wherein 40 channels are formed between the optodes. The optodes shown in FIG. 2 may be implemented as transmitter optodes of T1 to T13 and receiver optodes of R1 to R12. The optodes may cover an area controlling motion and an area controlling senses in the cerebral cortex.

In FIG. 2, each optode may function as a transmitter optode of T1 to T13 or as a receiver optode of R1 to R12. Each optode may include up to 4 neighbor channels around itself. For example, an optode 210 of R6 may receive a signal transmitted from an optode 220 of T7 through a channel S212 of CH20. Likewise, the channel 210 of R6 may receive signals transmitted from the optode 220 of T7, an optode 211 of T9, an optode 213 of T6, and an optode 214 of T4, and create the channel S212 of CH20, a channel S211 of CH24, a channel S213 of CH19, and a channel S214 of CH15. In this case, the neighbor channels of the optode 210 of R6 may be the channel S212 of CH20, the channel S211 of CH24, the channel S213 of CH19, and the channel S214 of CH15. Likewise, neighbor channels of the optode 220 of T7 may be a channel S221 of CH25, a channel S222 of CH21, a channel S223 of CH16, and the channel S212 of CH20.

According to an embodiment of the present disclosure, it may be possible to remove motion artifacts occurring at an arbitrary optode among N optodes disposed at a plurality of locations on the scalp based on a characteristic of an arrangement of the N optodes and channels.

According to an embodiment of the present disclosure, when various errors such as baseline drifting or baseline jumping occur at the optode 220 of T7, motion artifacts may occur at the channel S221 of CH25, the channel S222 of CH21, the channel S223 of CH16, and the channel S212 of CH20 which are the neighbor channels of the optode 220 of T7.

In this case, fNIRS signals of the channel S211 of CH24, the channel S213 of CH19, and the channel S214 of CH15 among the four channels around the optode 210 of R6 may be not affected by the motion artifacts, whereupon a fNIRS signal of the channel S212 of CH20 may be affected by the motion artifacts.

Figure 5:
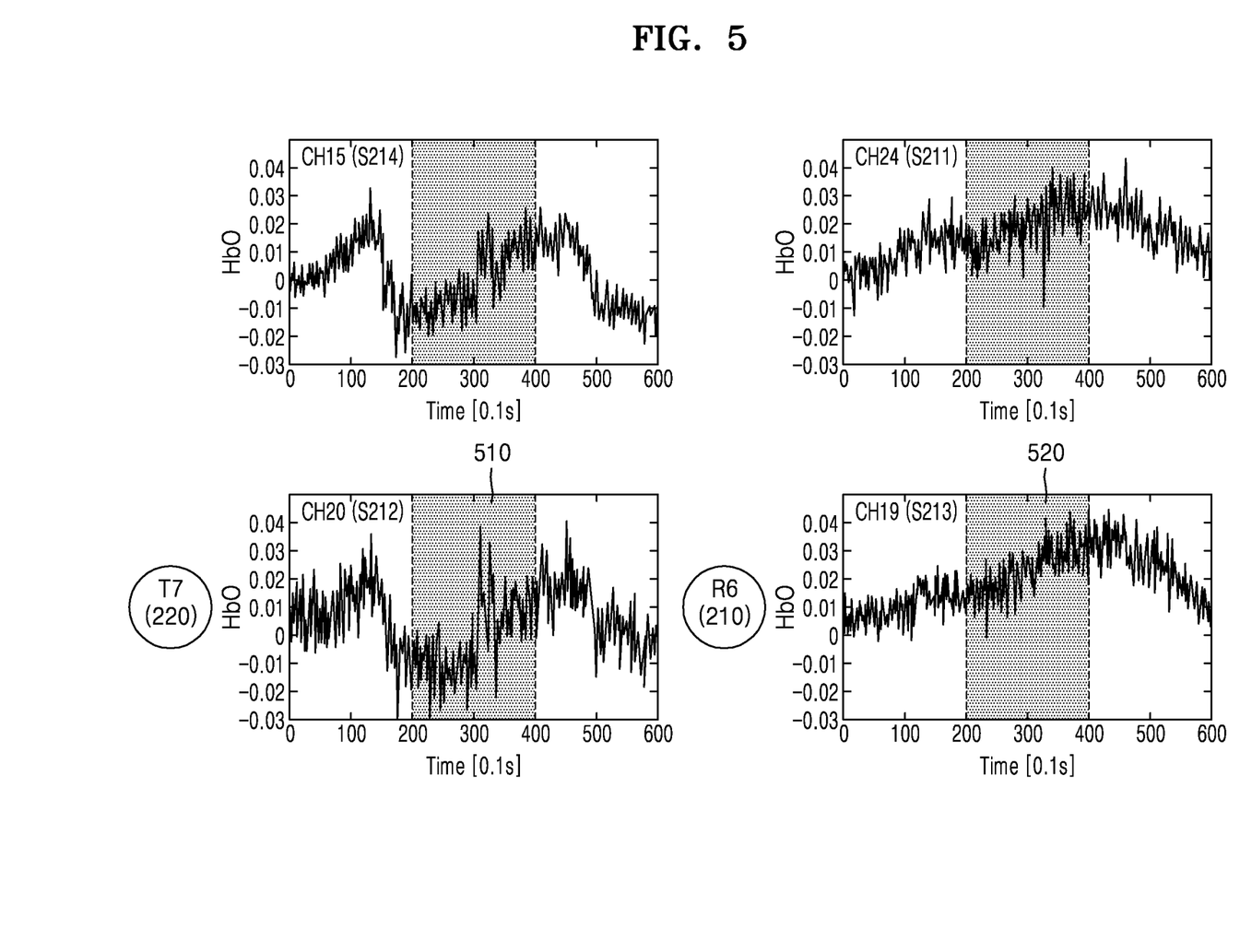
FIG. 5 shows an example of a channel at which motion artifacts occur, according to an embodiment of the present disclosure.

It is seen from FIG. 5 that motion artifacts are found in a section 200-400 of the channel S212 of CH20 that is adjacent to the optode 220 of T7, among the channels around the R6 optode 210, whereupon no motion artifact occurs in signal patterns of the channel S211 of CH24, the channel S213 of CH19, and the channel S214 of CH15 which are the neighbor channels of the optode 220 of T7.

In this case, in regard of entropy values of the channel S212 of CH20, the channel S211 of CH24, the channel S213 of CH19, and the channel S214 of CH15 around the R6 optode 210, the channel S211 of CH24, the channel S213 of CH19, and the channel S214 of CH15 may have similar entropy values, whereas the channel S212 of CH20 may have an entropy value that is different from those of the channel S211 of CH24, the channel S213 of CH19, and the channel S214 of CH15. Accordingly, when a fNIRS signal feature of the channel S212 of CH20 is different from those of the channel S211 of CH24, the channel S213 of CH19, and the channel S214 of CH15 around the channel S212 of CH20, it may be estimated that an error has occurred at the optode 210 of R6 or the optode 220 of T7 around the channel S212 of CH20. This will be described in more detail with reference to FIGS. 3 and 4.

Figure 3:
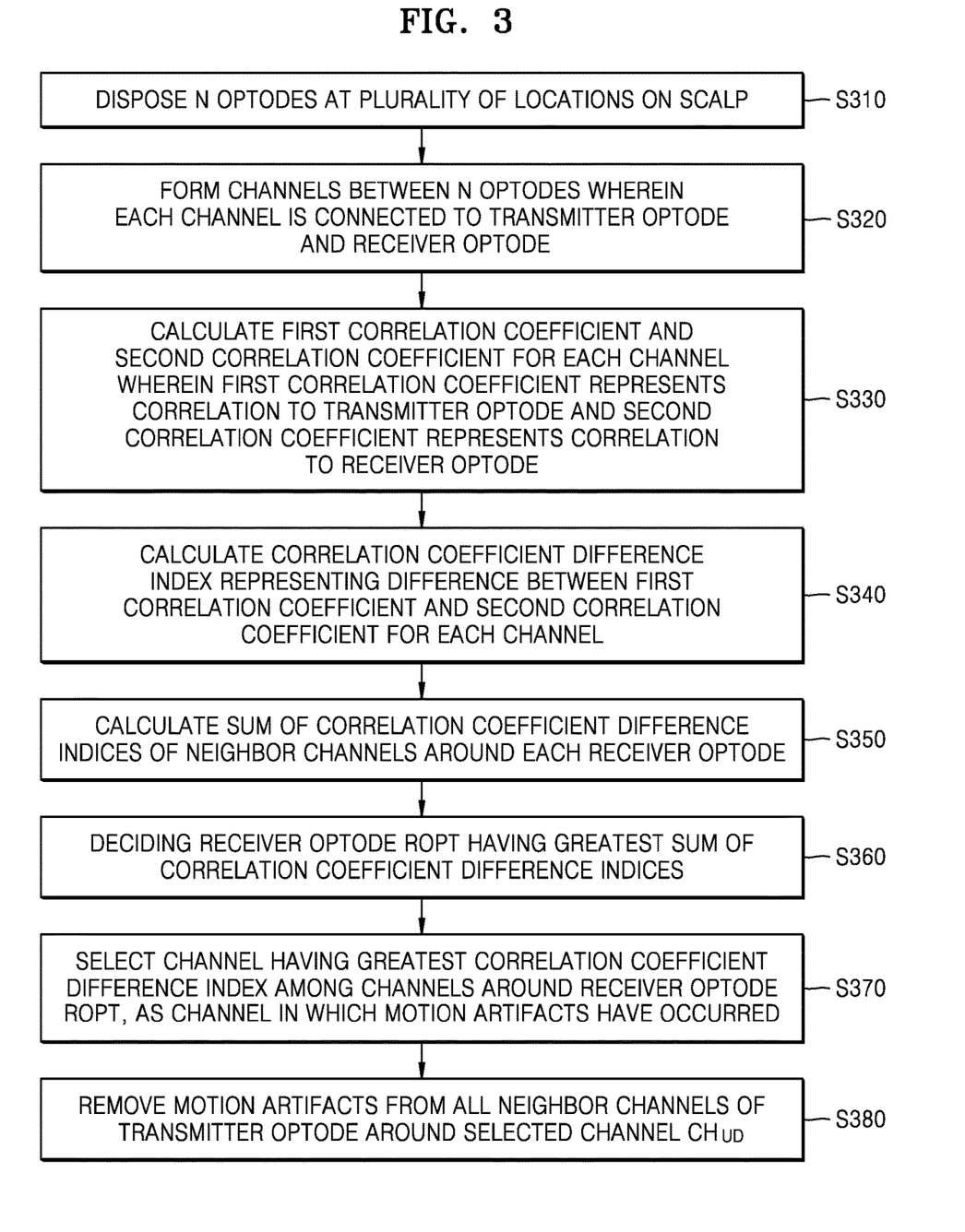
FIG. 3 is a flowchart illustrating a method of removing motion artifacts from multi-channel functional near-infrared spectroscopy (fNIRS) signals, according to an embodiment of the present disclosure.

FIG. 3 is a flowchart illustrating a method of removing motion artifacts from multi-channel fNIRS signals, according to an embodiment of the present disclosure.

According to an embodiment of the present disclosure, N optodes may be disposed at a plurality of locations on the scalp, in operation S310, and channels may be formed between the N optodes, in operation S320.

Thereafter, a first correlation coefficient and a second correlation coefficient for each channel may be calculated based on Equation 2, in operation S330, and a correlation coefficient difference index representing a difference between the first correlation coefficient and the second correlation coefficient may be calculated for each channel based on Equation 3, in operation S340.

Herein, the first correlation coefficient may represent a correlation between an entropy value of an arbitrary channel among neighbor channels around a transmitter optode and a mean value of entropy values of the remaining neighbor channels except for the arbitrary channel among the neighbor channels around the transmitter optode. Also, the second correlation coefficient may represent a correlation between an entropy value of an arbitrary channel among neighbor channels around a receiver optode and a mean value of entropy values of the remaining neighbor channels except for the arbitrary channel among the neighbor channels around the receiver optode.

Referring to FIG. 2, a first correlation coefficient of the channel S212 of CH20 among the channel S223 of CH16, the channel S212 of CH20, the channel S222 of CH21, and the channel S221 of CH25 around the optode 220 of T7 may be calculated as a correlation value between an entropy value of the channel S212 of CH20 and a mean value derived from a sum of entropy values of the channel S223 of CH16, the channel S222 of CH21, and the channel S221 of CH25. Likewise, a second correlation coefficient of the channel S212 of CH20 among the channel S214 of CH15, the channel S213 of CH19, the channel S212 of CH20, and the channel S211 of CH24 around the optode 210 of R6 may be calculated as a correlation value between the entropy value of the channel S212 of CH20 and a mean value derived from a sum of entropy values of the channel S214 of CH15, the channel S213 of CH19, and the channel S211 of CH24.

According to an embodiment of the present disclosure, entropy values for obtaining a first correlation coefficient and a second correlation coefficient may be calculated using Equation (1).

$$E = -\Sigma_{i=1}^{N} a(i) \log_2 |a(i)| \quad (1)$$

In Equation (1), a(i) represents a signal of an i-th channel, and N represents the number of samples.

According to an embodiment of the present disclosure, an entropy value ($E_{Hbo}^{ch}(n)$) of a n-th sample for a specific channel may be calculated using a sample appearing one second (−N/2) before a fNIRS signal y(n) and a sample appearing one second (+N/2) after the fNIRS signal y(n).

Also, a mean entropy ($E_{Hbo}^{-opt}(n)$) for a specific optode represents a mean value of entropy values of all channels connected to the optode with respect to the same time n.

$$\Gamma_{Opt_{typ}}^{ch} = \sum_{i=1}^{N} E_{HbO}^{ch}(i) E_{HbO}^{Opt}(i) \quad (2)$$

$$UD^{ch} = |\Gamma_{Opt_T}^{ch} - \Gamma_{Opt_R}^{ch}| \quad (3)$$

Equation (3) represents a correlation coefficient difference index. When neighbor channels around an optode have different features and a low correlation, the optode may have a great correlation coefficient difference index.

After the correlation coefficient difference index for each channel is calculated based on Equation 3 in operation S340, a sum of correlation coefficient difference indices of neighbor channels of each receiver optode may be calculated in operation S350. Then, a receiver optode Ropt having a greatest sum of correlation coefficient difference indices may be decided, in operation S360. Thereafter, a channel having a greatest correlation coefficient difference index among channels around the receiver optode Ropt may be selected as a channel at which a motion artifact has occurred, in operation S370.

According to an embodiment of the present disclosure, motion artifacts may be removed from all neighbor channels of a transmitter optode around a channel $CH_{UD}$ having a greatest correlation coefficient difference index, in operation S380. For example, referring to FIG. 2, when the optode 210 of R6 is calculated as an optode having a greatest correlation coefficient difference index, a channel having a greatest correlation coefficient difference index may be selected from among the channel S212 of CH20, the channel S211 of CH24, the channel S213 of CH19, and the channel S214 of CH15 around the optode 210 of R6. For example, when the channel S212 of CH20 has a greatest correlation coefficient difference index, motion artifacts may be removed from all the neighbor channels (that is, the CH26 channel S223, the channel S212 of CH20, the channel S222 of CH21, and the channel S221 of CH25) of the optode 220 of T7 around the channel S212 of CH20.

Figure 4:
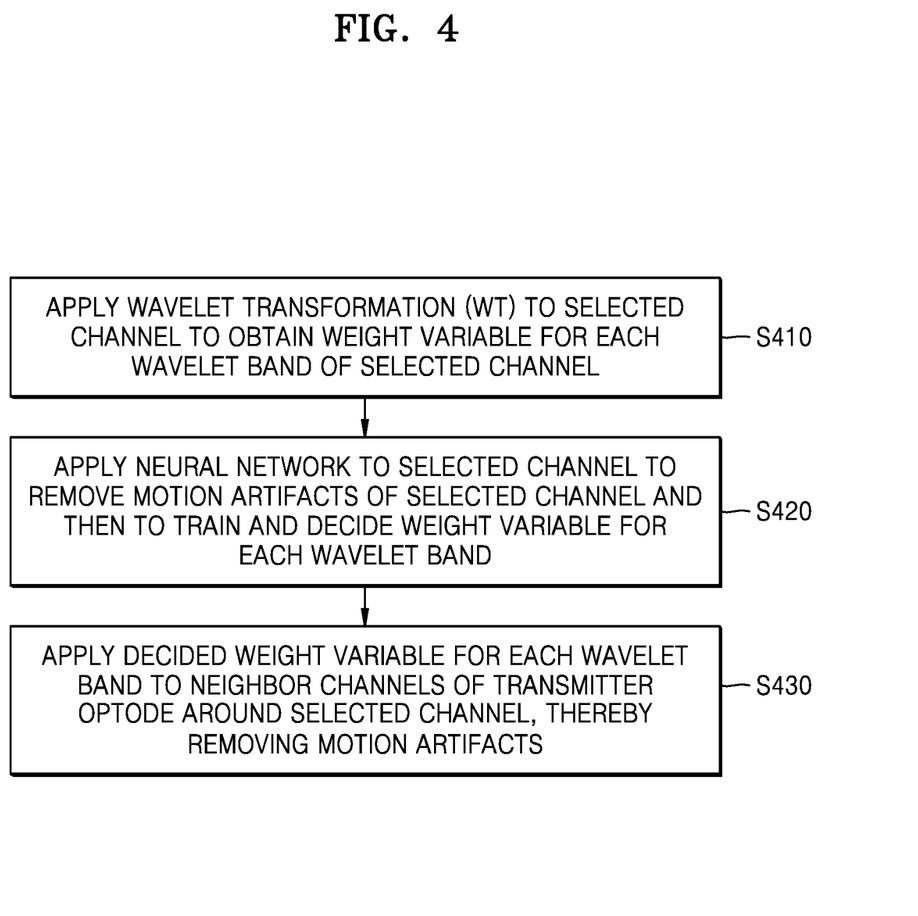
FIG. 4 is a detailed flowchart illustrating a method of removing motion artifacts from multi-channel fNIRS signals, according to an embodiment of the present disclosure.
Figure 6:
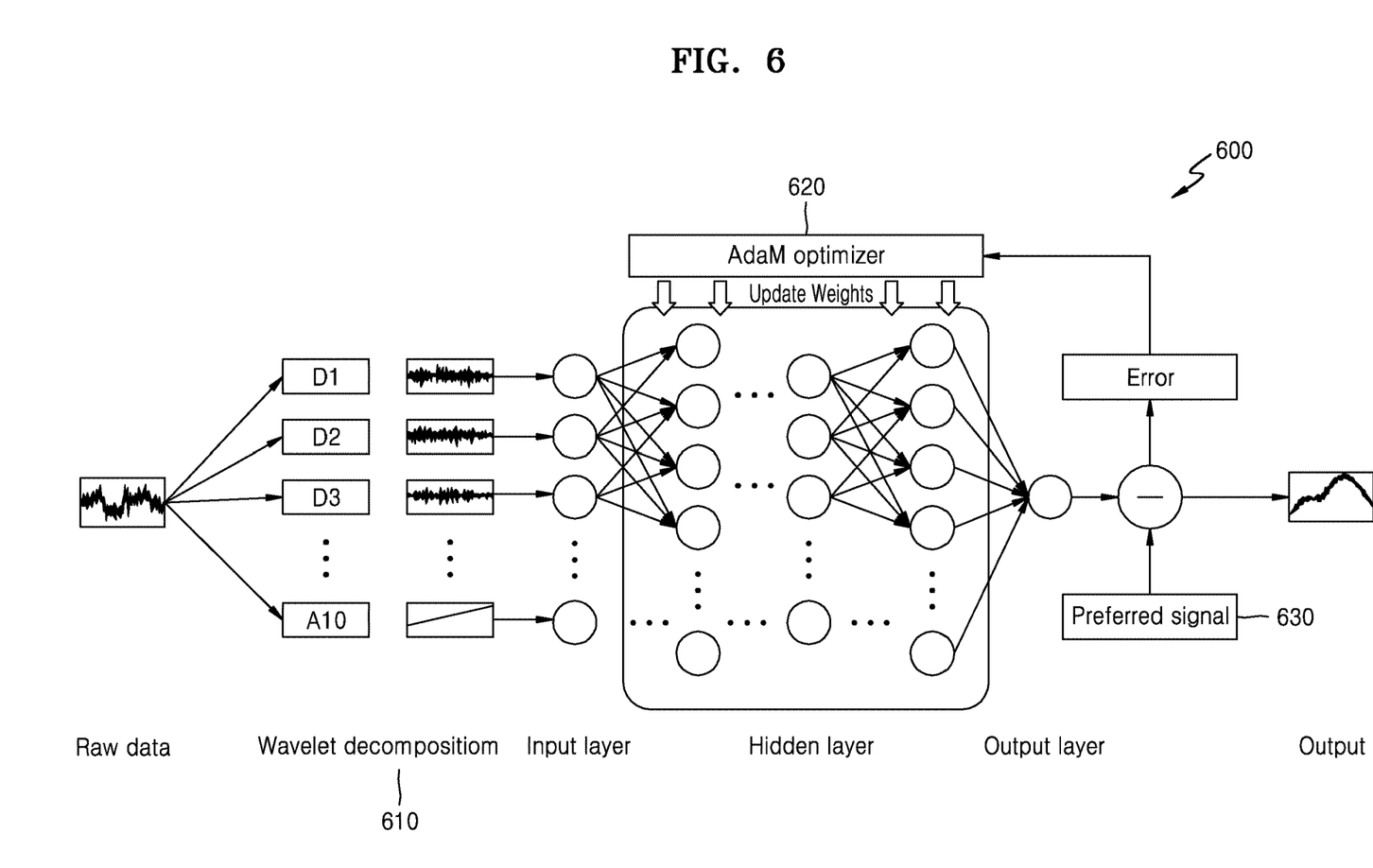
FIG. 6 is a detailed block diagram of a motion artifact remover for removing motion artifacts, according to an embodiment of the present disclosure.

FIG. 4 is a detailed flowchart illustrating a method of removing motion artifacts from multi-channel fNIRS signals, according to an embodiment of the present disclosure. FIG. 6 is an internal block diagram of a motion artifact remover. Hereinafter, a process of removing motion artifacts will be described with reference to FIGS. 4 and 6.

According to an embodiment of the present disclosure, wavelet transformation (WT) may be used to remove motion artifacts from multi-channel fNIRS signals. According to an embodiment of the present disclosure, wavelet transformation may be applied to the channel $CH_{UD}$ having the greatest correlation coefficient difference index, selected by the method shown in FIG. 3, to obtain a weight variable for each wavelet band of the channel $CH_{UD}$, in operation S410. Then, a neural network may be applied to the channel $CH_{UD}$ having the greatest correlation coefficient difference index to remove motion artifacts of the channel $CH_{UD}$ and then to train and decide a weight variable for each wavelet band of the channel $CH_{UD}$, in operation S420. Thereafter, the decided weight variable for each wavelet band may be applied to wavelet variables obtained by wavelet-transforming neighbor channels of a transmitter optode around the channel $CH_{UD}$, thereby removing motion artifacts, in operation S430.

According to an embodiment of the present disclosure, a weight variable $w_{j,m}(k)$ for each wavelet band may be calculated according to Equation (4). An initial value of the weight variable $w_{j,m}(k)$ may be set to an arbitrary value, and then a trainer (see 620 of FIG. 6) may perform training based on an error value between a preferred signal (see 630 of FIG. 6) and an output value, in operation S430.

Referring to FIG. 2, when the channel S212 of CH20 is selected as a channel having a greatest correlation coefficient difference index, the preferred signal 630 may be a mean value of entropy of the channel S211 of CH24, the channel S213 of CH19, and the channel S214 of CH15 having similar entropy signal features.

$$w_{j,m}(k)=WT[y(n),j] \quad (4)$$

In Equation (4), WT represents wavelet transformation, y(n) represents a fNIRS signal of the channel $CH_{UD}$, j represents the number of levels by which wavelet transformation is performed, and k represents a k-th wavelet variable of a m-th sub-band.

For example, the fNIRS signal may be decomposed to 11 sub-bands of the wavelet coefficient $w_{j,m}(k)$ by using 10-level wavelet transformation. In this case, j=1, 2, ..., 10, m=1, 2, ..., 11, and k=1, 2, ..., N/2j.

Referring to FIG. 6, a wavelet transformer 610 may perform wavelet transformation on a fNIRS signal, and the trainer 620 may perform training to obtain a most appropriate weight variable for each wavelet band.

The trainer 620 may distinguish tasks that cannot be easily distinguished from each other, such as baseline jumping and rapid head movements, and train the tasks. For this, the trainer 630 may perform machine training using a back propagation neural network (BPNN), feed forward neural networks (FFNN), etc. The machine training may include pattern recognition, pattern classification, etc. According to an embodiment of the present disclosure, the trainer 620 may also perform training to correct noise including motion artifacts using the BPNN.

The trainer 620 may train a weight variable $w_{j,m}(k)$ for each wavelet band of the channel CHuo having the greatest correlation coefficient difference index through machine training, and decide the weight variable $w_{j,m}(k)$.

Thereafter, the weight variable $w_{j,m}(k)$ trained and decided for the channel $CH_{UD}$ having the greatest correlation coefficient difference index through the trainer 620 may be applied as a weight variable of neighbor channels of a transmitter optode around the channel $CH_{UD}$ having the greatest correlation coefficient difference index, thereby removing motion artifacts occurred at the neighbor channels around the transmitter optode.

Figure 7:
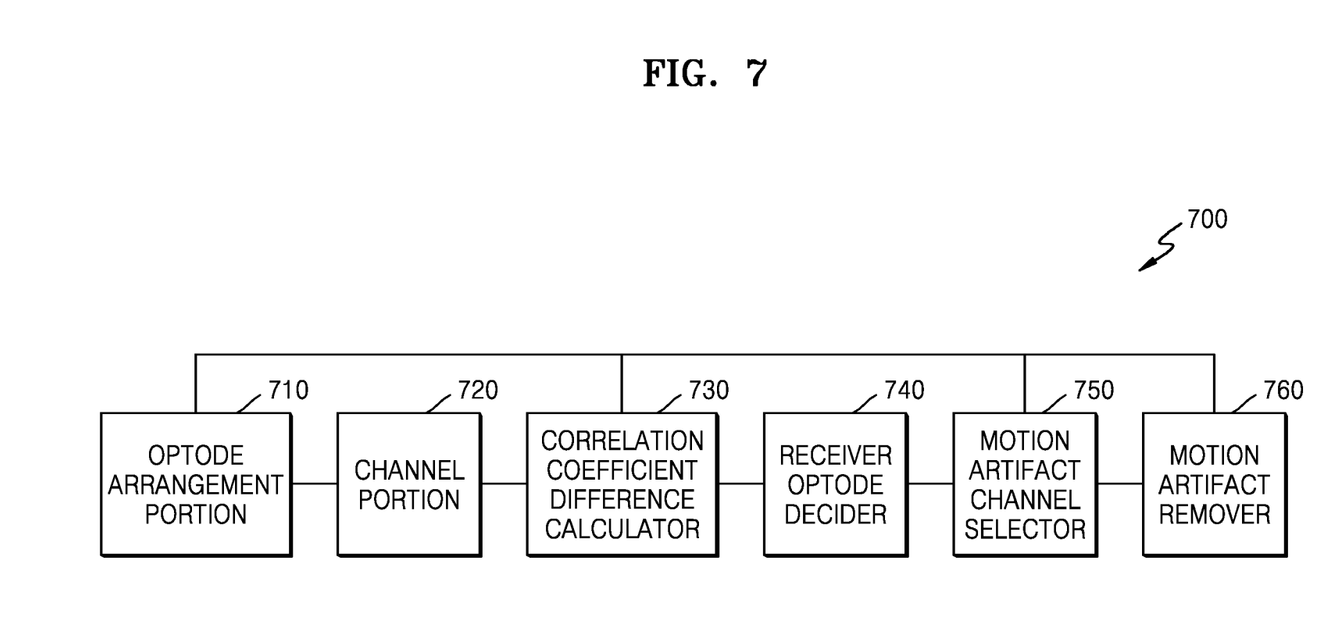
FIGS. 7 and 8 are internal block diagrams of an apparatus for removing motion artifacts from multi-channel fNIRS signals, according to an embodiment of the present disclosure.

FIG. 7 is an internal block diagram of an apparatus for removing motion artifacts from multi-channel fNIRS signals, according to an embodiment of the present disclosure.

An apparatus 700 for removing motion artifacts from multi-channel fNIRS signals may include an optode arrangement portion 710, a channel portion 720, a correlation coefficient difference calculator 730, a receiver optode decider 740, a motion artifact channel selector 750, and a motion artifact remover 760.

The optode arrangement portion 710 may arrange N optodes at a plurality of locations on the scalp, and the channel portion 720 may form a plurality of channels between the N optodes.

The correlation coefficient difference calculator 730 may calculate a first correlation coefficient and a second correlation coefficient for each channel. Then, the correlation coefficient difference calculator 730 may calculate a correlation coefficient difference index which is a difference between the first correlation coefficient and the second correlation coefficient.

The receiver optode decider 740 may calculate a sum of correlation coefficient difference indices of neighbor channels of each receiver optode, and decide a receiver optode Ropt having a greatest sum of correlation coefficient difference indices among the receiver optodes disposed on the scalp.

The motion artifact channel selector 750 may select a channel having a greatest correlation coefficient difference index from among channels around the receiver optode Ropt, as a channel at which a motion artifact has occurred. The motion artifact remover 760 may remove motion artifacts from all neighbor channels of a transmitter optode around the channel selected by the motion artifact channel selector 750.

Figure 8:
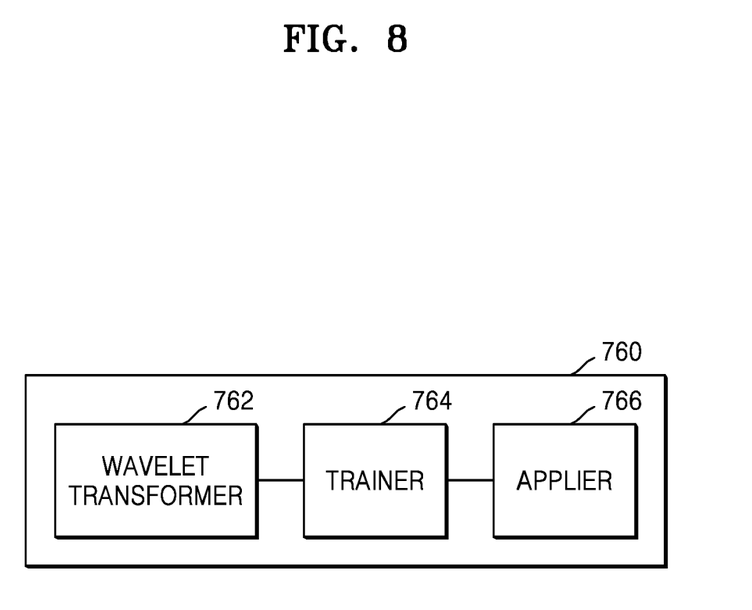

FIG. 8 is a block diagram of a motion artifact remover according to an embodiment of the present disclosure.

The motion artifact remover 760 may include a wavelet transformer 762, a trainer 764, and an applier 766. The wavelet transformer 762 may perform wavelet transformation on a channel having a greatest correlation coefficient difference index among the channels around the receiver optode Ropt to obtain a weight variable for each wavelet band of the channel having the greatest correlation coefficient difference index. The trainer 764 may train a weight variable for each wavelet band using a neural network in order to remove motion artifacts from the channel having the greatest correlation coefficient difference index, and decide a final weight variable. The applier 766 may store the final weight variable as a weight variable model, and apply the stored weight variable model to the neighbor channels of the transmitter optode around the channel having the greatest correlation coefficient difference index to remove motion artifacts.

According to an embodiment of the present disclosure, when motion artifacts occur, a highly unbalanced optode may be detected from among optodes using an arrangement structure of the optodes to find an optode at which the highest motion artifact has occurred, and then motion artifacts may be removed from channels around the found optode.

According to an embodiment of the present disclosure, by finding an optode at which the highest motion artifact has occurred, and removing the motion artifact occurred at the found optode, it may be possible to overcome a problem of attenuating or distorting a hemodynamic response signal component of a channel signal in which no motion artifact occurs. Also, it may be possible to overcome a problem of determining a hemodynamic response component by a task as a motion artifact component and thus removing the hemodynamic response component in a single task-based experimental environment.

The proposed method may be implemented as computer-readable code in a computer-readable recording medium. The computer-readable recording medium may include any kind of recording device storing computer-readable data. Examples of the recording medium may include Read Only Memory (ROM), Random Access Memory (RAM), optical disk, magnetic tape, floppy disk, hard disk, non-volatile memory, and the like, and may also include the medium that is implemented in the form of carrier waves (for example, transmission over the Internet). In addition, the computer-readable recording medium may be distributed over the computer systems connected over the network, and computer-readable codes may be stored and executed in a distributed manner.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of removing motion artifacts from a multichannel functional near-infrared spectroscopy (fNIRS) signal, comprising:
    disposing N optodes at a plurality of locations on a scalp;
    forming a plurality of channels between the N optodes, wherein each channel is connected to a transmitter optode and a receiver optode;
    calculating a first correlation coefficient and a second correlation coefficient for each channel, wherein the first correlation coefficient represents a correlation of the channel to the transmitter optode and the second correlation coefficient represents a correlation of the channel to the receiver optode;
    calculating a correlation coefficient difference index which is a difference between the first correlation coefficient and the second correlation coefficient, for each channel;
    calculating a sum of correlation coefficient difference indices of neighbor channels of each receiver optode;
    deciding a receiver optode Ropt having a greatest sum of correlation coefficient difference indices;
    selecting a channel having a greatest correlation coefficient difference index among channels around the receiver optode Ropt, as a channel in which a motion artifact has occurred; and
    removing motion artifacts from all neighbor channels of a transmitter optode around the selected channel.

2. The method according to claim 1, wherein the removing of the motion artifacts comprises:
    performing wavelet transformation on the selected channel to obtain a weight for each wavelet band of the channel;
    applying a neural network to the selected channel to remove motion artifacts from the selected channel, and then training and deciding a weight for each wavelet band of the channel; and
    applying the decided weight variable for each wavelet band to neighbor channels of a transmitter optode around the selected channel, thereby removing motion artifacts.

3. The method according to claim 1, wherein the first correlation coefficient and the second correlation coefficient are calculated based on an entropy value of each channel.

4. The method according to claim 1, wherein the first correlation coefficient represents a correlation between an entropy value of an arbitrary channel among neighbor channels around a transmitter optode and a mean value of entropy values of the remaining neighbor channels except for the arbitrary channel among the neighbor channels around the transmitter optode, and
    the second correlation coefficient represents a correlation between an entropy value of an arbitrary channel among neighbor channels around a receiver optode and a mean value of entropy values of the remaining neighbor channels except for the arbitrary channel among the neighbor channels around the receiver optode.

5. A method of removing motion artifacts from a multichannel functional near-infrared spectroscopy (fNIRS) signal, comprising:
    disposing N optodes at a plurality of locations on a scalp;
    forming a plurality of channels between the N optodes;
    calculating a correlation coefficient difference index of a neighbor channel around each receiver optode, and detecting a receiver optode in which a motion artifact has occurred based on the correlation coefficient difference index; and
    removing motion artifacts based on the detected receiver optode and an arrangement structure of the N optodes.

6. The method according to claim 5, wherein the correlation coefficient difference index is calculated for each channel, the correlation coefficient difference index represents a difference index between a first correlation coefficient and a second correlation coefficient, the first correlation coefficient represents a correlation of the channel to a transmitter optode and the second correlation coefficient represents a correlation of the channel to a receiver optode.

7. The method according to claim 5, wherein a channel $CH_{UD}$ having a greatest correlation coefficient difference index among neighbor channels around the detected receiver optode is selected as a channel in which a motion artifact has occurred.

8. The method according to claim 5, wherein the removing of the motion artifacts comprises removing motion artifacts from all neighbor channels of a transmitter optode around the selected channel $CH_{UD}$.

9. The method according to claim 8, wherein the removing of the motion artifacts comprises:
    performing wavelet transformation on the channel $CH_{UD}$ to obtain a weight value for each wavelet band of the channel $CH_{UD}$;
    applying a neural network to the selected channel $CH_{UD}$ to remove a motion artifact of the selected channel, and then training and deciding a weight value for each wavelet band of the channel $CH_{UD}$; and
    applying the decided weight variable for each wavelet band to neighbor channels of a transmitter optode around the selected channel $CH_{UD}$, thereby removing motion artifacts.

10. An apparatus of removing motion artifacts from a multi-channel functional near-infrared spectroscopy (fNIRS) signal, the apparatus comprising:
- an optode arrangement portion configured to dispose N optodes at a plurality of locations on a scalp;
- a channel portion configured to form a plurality of channels between the N optodes, wherein each channel is connected to a transmitter optode and a receiver optode;
- a correlation coefficient difference calculator configured to calculate a first correlation coefficient and a second correlation coefficient for each channel, and configured to calculate a correlation coefficient difference index which is a difference between the first correlation coefficient and the second correlation coefficient, for each channel, wherein the first correlation coefficient represents a correlation of the channel to the transmitter optode and the second correlation coefficient represents a correlation of the channel to the receiver optode;
- a receiver optode decider configured to calculate a sum of correlation coefficient difference indices of neighbor channels around each receiver optode, and to decide a receiver optode Ropt having a greatest sum of correlation coefficient difference indices;
- a motion artifact channel selector configured to select a channel having a greatest correlation coefficient difference index among channels around the receiver optode Ropt, as a channel in which a motion artifact has occurred; and
- a motion artifact remover configured to remove motion artifacts from all neighbor channels of a transmitter optode around the selected channel.

11. The apparatus according to claim 10, wherein the motion artifact remover comprises:
- a wavelet transformer configured to perform wavelet transformation on the selected channel to obtain a weight variable for each wavelet band of the channel;
- a trainer configured to apply a neural network to the selected channel to remove a motion artifact of the selected channel, and then to train and decide a weight variable for each wavelet band of the channel; and
- an applier configured to apply the decided weight variable for each wavelet band to neighbor channels of a transmitter optode around the selected channel, thereby removing motion artifacts.

* * * * *